United States Patent [19]
Zimmerman et al.

[11] 4,100,166
[45] * Jul. 11, 1978

[54] NOVEL CIS N-CYCLOPROPYLMETHYL DECAHYDROISOQUINOLINE

[75] Inventors: Dennis M. Zimmerman, Mooresville; Winston S. Marshall, Bargersville, both of Ind.

[73] Assignee: Eli Lilly and Company, Indianapolis, Ind.

[*] Notice: The portion of the term of this patent subsequent to Jan. 4, 1994, has been disclaimed.

[21] Appl. No.: 734,895

[22] Filed: Oct. 22, 1976

Related U.S. Application Data

[63] Continuation-in-part of Ser. No. 477,222, Jun. 7, 1974, Pat. No. 4,001,248.

[51] Int. Cl.² .................. C07D 217/04; A61K 31/47

[52] U.S. Cl. .................. 260/289 D; 424/258; 260/286 R

[58] Field of Search .................. 260/289 D, 286 R

[56] References Cited

U.S. PATENT DOCUMENTS 4,001,248  1/1977  Zimmerman et al. .......... 260/289 D

FOREIGN PATENT DOCUMENTS 802,557  7/1973  Belgium .................. 260/289 D

*Primary Examiner*—Donald G. Daus
*Assistant Examiner*—Mary Vaughn
*Attorney, Agent, or Firm*—James L. Rowe; Arthur R. Whale

[57] ABSTRACT

Cis-1-cyclopropylmethyl-3a-(substituted-phenyl) decahydroisoquinoline, useful as analgetic agonist and analgetic antagonist.

2 Claims, No Drawings

NOVEL CIS N-CYCLOPROPYLMETHYL DECAHYDROISOQUINOLINE

CROSS-REFERENCE

The application is continuation-in-part of our copending application Ser. No. 477,222 filed Jun. 7, 1974, now U.S. Pat. No. 4,001,248 issued Jan. 4, 1977.

BACKGROUND OF THE INVENTION

It has long been known that slight chemical modifications of the morphine molecule lead to analgesic agonists of widely differing potency and addictive properties. For example, codeine, the methyl ether of morphine, is a relatively mild analgesic agonist having slight dependance (addiction) liability. On the other hand, heroin, the diacety derivative of morphine, is a powerful agonist with extremely high addiction potential. In addition, as long ago as 1915, Pohl found that when the N-methyl group of codeine was replaced with an allyl group, the resulting compound, N-allylnorcodeine, was an opiate antagonist. In 1940, N-allylnormorphine or nalorphine was synthesized and was shown to have a highly specific ability to reverse the depressant effects of morphine. Other simple chemical modifications of the morphine molecule have yielded many interesting drugs. Thus, one fruitful research area in the search for improved analgesics of high potency and/or lower dependance (addiction) liability has been the chemical modification of the morphine molecule.

In addition to modifying the morphine ring structure by chemical means, chemists have developed a second related field of research--the preparation of certain mrophine part-structures--with the same end in mind as above; i.e., the synthesis of improved analgesic agonists and/or analgesic antagonists of improved properties. For example, meperidine, a widely used analgesic, can be written as a morphine part-structure. Many other morphine part-structures have been prepared, some of which have improved analgesic agonist properties and others, particularly those with an allyl group attached to a ring nitrogen, have opiate antagonist properties. It had been hoped that morphine part-structure research would produce a compound having both opiate agonist and antagonist properties since the opiate antagonist property would assure a user that the compound would have a greatly reduced dependance liability. Two recently marketed analgesics, pentazocine and phenazocine, have been found to be both antagonists and agonists although they still retain a certain degree of opiate dependance liability.

One potential morphine part-structure can be written as a decahydroisoquinoline with an hydroxyphenyl group substituted on a ring junction carbon atom para to the isoquinoline nitrogen. An attempt to prepare such a compound was described by Boekelheide in a paper appearing in *J. Am. Chem. Soc.*, 69, 790 (1947). This paper set forth the preparation of what, according to the numbering system then in vogue, were 10-phenyl-decahydroisoquinolines. It was the author's conclusion, however, that the compound (IX) had a cis configuration and (footnote 5) showed low analgesic activity. The synthesis itself is cumbersome and not free from ambiguity. Sugimoto et. al., *J. Pharm. Soc. Japan*, 75 177 (1955), C. A. 1956 1814b described the synthesis of 8 or 10-alkylated decahydroquinolines. The reference also shows the morphine part-structure, 10-(m-hydroxyphenyl)-3-methylisoqyinoline [presently named as 1-methyl-3a-(m-hydroxyphenyl)-1,2,3,3a,4,5,6,7,7a,8-decahydroisoquinoline] but without furnishing a synthesis for it. These authors do not, in fact, describe the preparation of any decahydroisoquinoline analogs.

Belgian Pat. No. 802,557, issued Jan. 19, 1974, discloses a general method of preparing N-substituted trans-dl-3a-phenyldecahydroisoquinolines and specifically discloses trans-dl-3a-(m-methoxy phenyl) and trans-3a-(m-hydroxyphenyl)-1-methyldecahydroisoquinolines, trans-dl-3a-(m-methoxyphenyl) and trans-dl-3a-(m-hydroxyphenyl)-1-phenethyldecahydroisoquinoline. The synthetic procedure employed involves the catalytic reduction of the 7-7a double bond in, for example, a 1-alkyl-3a-phenyl (or substituted phenyl) substituted phenyl) 1,2,3,3a,4,5,6,8-octahydroisoquinoline. No new procedure for preparing the cis racemate is given.

Finch and coworkers, *J. Org. Chem.*, 39, 1118 (1974) disclose trans-dl-1-methyl-3a-phenyl-1,2,3,3a,4,5,7a,8-octahydroisoquinoline (formula 2d, page 1119) and prepared by an independant route the corresponding cis-dl-1-methyl-3a-phenyldecahydroisoquinoline compound (formula 26, page 1120), the compound allegedly prepared by Boekelheide (loc. cit) - see also Boekelheide and Schilling, *J. Am. Chem. Soc.*, 72 712 (1950). Finch et al., from a comparison of their cis racemate and a sample of the Bockelheide and Schilling preparation concluded that these latter workers had in fact prepared the trans racemate. However, no one has as yet repeated the Bockelheide and Schilling preparation. Finch et al. use a different numbering system for the isoquinoline ring, using a naphthalene-type numbering rather than designating the ring nitrogen as position 1, and number their compounds as 2-methyl-4a-phenyl-6-hydroxy derivatives.

SUMMARY OF THE INVENTION

This invention provides cis-dl-1-cyclopropylmethyl-3a-(m-hydroxyphenyl)-1,2,3,3a,4,5,6,7,7a,8-decahydroisoquinoline of the formula

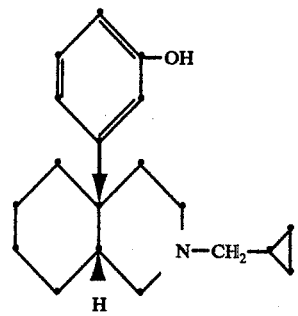

Also included within the scope of this invention are pharmaceutically-acceptable acid addition salts of the above base formed with non-toxic acids. The pharmaceutically acceptable salts of the amine base represented by the above formula are formed with non-toxic acids, such as hydrochloric acid, nitric acid, phosphoric acid, sulfuric acid, hydrobromic acid, hydriodic acid, nitrous acid, phosphorous acid and the like, as well as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monhydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and the like salts.

In 3a-phenyldecahydroisoquinolines of the type illustrated above, the bridehead substituents, the metahydroxyphenyl at 3a and the hydrogen at 7a, have a cis relationship to one another; i.e., the two substituents are on the same "side" of the decahydroisoquinoline ring system (cis) as opposed to being an opposite "sides" (trans). In addition, both the 3a and 7a carbon atoms are asymmetric, thus giving rise to 2 optical isomers, occurring as a racemate designated as the cis-dl pair.

The compound of this invention is prepared according to the following procedure:

2-(2-Cyanoethyl)-2-(m-methoxyphenyl) cyclohexanone, prepared by the method of Boekelheide, *J. Am. Chem. Soc.*, 69, 790 (1947), is hydrolysed to 2-(2-carboxyethyl)-2-(m-methoxyphenyl) cyclohexanone. The free acid thus formed is reacted with ethyl chloroformate in the presence of triethylamine to yield the acid anhydride which is in turn reacted with sodium azide. The product of this reaction, an acyl azide, is decomposed under conditions which promote the Curtius rearrangememt to yield an isocyanate which, upon refluxing with aqueous acid yields an imine of Structure III. This reaction sequence is illustrated below:

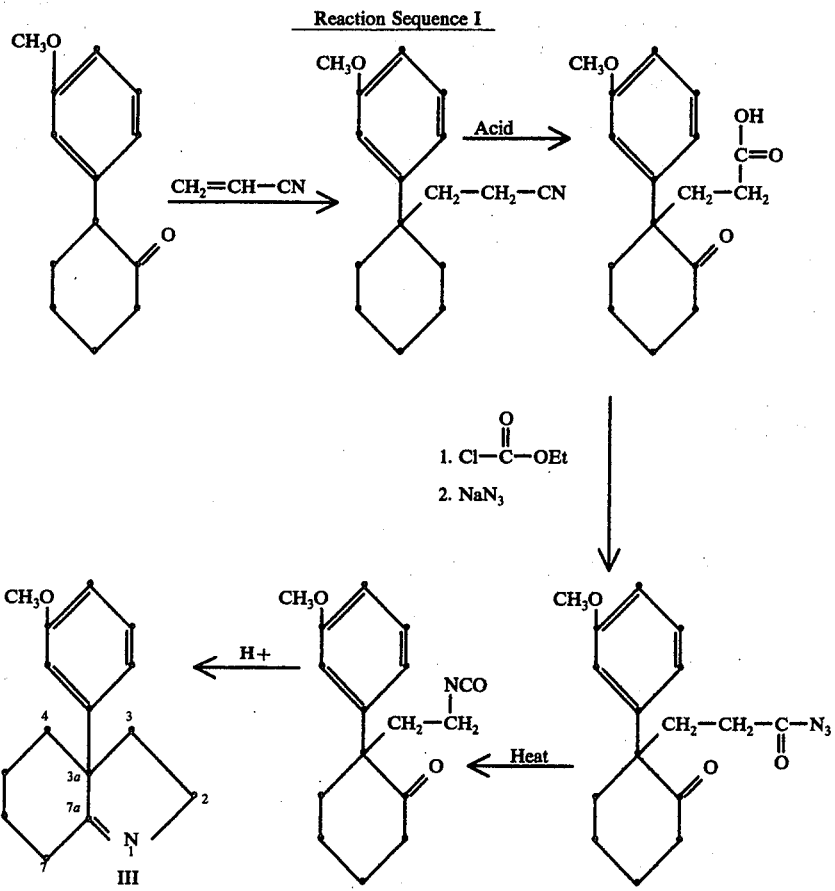

Reaction Sequence I

In carrying out the chemical transformations delineated in Reaction Sequence I, we prefer to hydrolyze the nitrile function of 2-(β-cyanoethyl)-2-(m-methoxyphenyl)-cyclohexanone using a mineral acid in a strongly acidic medium; for example, 12N aqueous hydrochloric acid in 60–70 percent aqueous acetic acid. Other mineral acids such as sulfuric and phosphoric may also be used, as can a purely aqueous reaction medium, without affecting the yield or purity of the product in any way. Alkaline hydrolysis may also be used, but it is necessary to use somewhat more stringent reaction conditions in order to carry the hydrolysis past the intermediate amide stage to the free acid. Higher boiling inert solvents such as diethyleneglycol can be used. The next step of the reaction sequence, the formation of an acid anhydride from the carboxylic acid of the previous step, can be accomplished by the use of ethyl chloroformate. An acid chloride can also be formed by reaction with thionyl chloride etc. An acid acceptor such as triethylamine can also be used to advantage in forming an acid anhydride or acid chloride, using an inert solvent. The reaction of the thus formed acid anhydride with sodium azide to form the acid azide is carried out under standard conditions. It should be recognized, however, that an alternate procedure for preparing the azide exists; i.e., the formation of the hydrazide by reaction of anhydrous hydrazine with the acid chloride followed by azide formation with nitrous acid. Rearrangement of the azide under Curtius rearrangement conditions, consisting simply in heating the azide, however synthesized, at the reflux temperature of benzene or toluene for from 1 to about 24 hours, yields the expected isocyanate. Acidification of the isocyanate product yields directly a 3H-indole (III). The acidification is carried out by heating the isocyanate with a concentrated mineral acid as for example hydrochloric or sulfuric acid for from 12–24 hours. The product, as the free base, is isolated by basifying the acid reaction medium with, for example, sodium hydroxide, sodium carbonate or the like.

Structure III above is named 3a-(m-methoxyphenyl)-3H-indole or 3a-(m-methoxyphenyl)-3H-benzo[b]pyrrole and has also been prepared by Langlois et al. *Tetrahedron*, 27, 6541 (1971) using a different method of synthesis.

Reaction Sequence 2 below outlines one procedure for the production of an intermediate useful in preparing the compound of this invention, from the intermediates of Reaction Sequence I. The 3H-indole (III) end product of Reaction Sequence I is methylated quantitatively to yield an iminium salt (IIIa) which compound is next reacted, also quantitatively, with diazomethane to yield an aziridinium salt (IV). The aziridinium salt rearranges to produce a mixture of double-bond isomers (Va and Vb). Reduction of the enamine isomer (Va) with sodium borohydride in acetic acid yields a decahydroisoquinoline-VI or VIa.

The trans-dl-racemate, (VI), is the predominant racemate isolated from this reaction with only minor quantities of the cis-dl-racemate (VIa) being formed. Platinum hydrogenation also yields predominantly the trans-dl-racemate. On the other hand, hydrogenation of the enamine (Va) with 5 percent palladium-on-carbon yields a mixture of the cis-dl- and trans-dl racemates (40–60), which racemates are readily separated from each other by precipitating the trans-dl racemate as a picrate salt. The cis-dl racemate does not form an insoluble picrate and remains in the filtrate. The above series of reactions is illustrated below in Reaction Sequence II:

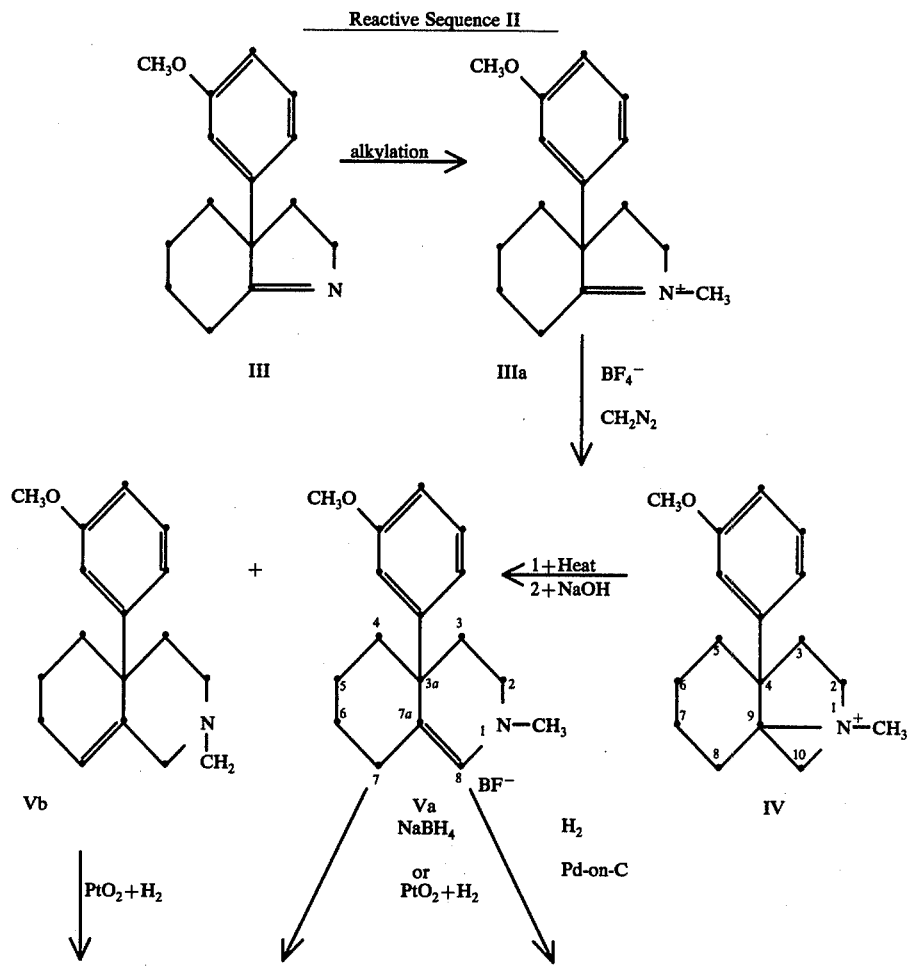

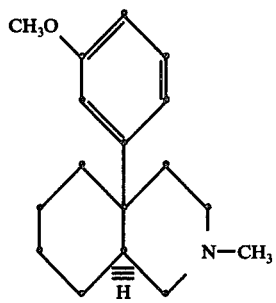

VI

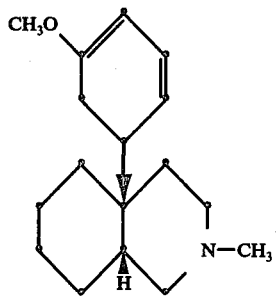

VIa

In carrying out the procedures outlined in Reaction Sequence II above, alkylation of the 3H-indole (III) to yield the quaternary methyl derivative (IIIa) is carried out preferably by treating the indole with trimethyloxonium tetrafluoroborate. Other alkylating agents can, however, be used as for example dimethyl sulfate, methyl iodide and the like. The product of this methylation reaction, an iodide or sulfate salt, is then metathesized to the fluoroborate salt by reaction with fluoroboric acid. Transformation of this quaternary salt to an aziridinium salt (IV) named systematically as a salt of 1-azonia-1-methyl-4-(m-methoxyphenyl)tricyclo [4,2,1,0$^{1-9}$] decane), is accomplished by reacting the iminium salt with diazomethane. The diazomethane can be generated in situ or added as a solution in accordance with procedures long established in the art. The aziridinium salt is rearranged to yield a mixture of double-bond isomers (Va and Vb) (85-15) by heating, preferably for about 1 hour at about 200° C. although longer reaction times at somewhat lower temperatures will give essentially the same yields. The direct product of the rearrangement is an amine salt which must be treated with a base such as sodium hydroxide or sodium carbonate in order to provide the N-methyl octahydroisoquinolines (Va and Vb) as free bases. The reduction of the (Va and Vb) to the corresponding decahydroisoquinolines (VI and VIa) has been discussed above.

The preparation of compounds according to Formula I can be accomplished as follows. As a starting point, the N-methyl derivative (VIa above) is reacted with phenylchloroformate to yield a carbamate.

Hydrolysis of this carbamate provides the secondary amine. Alkylation of the secondary amine by standard procedures using a suitable cyclopropyl halide readily yields the m-methoxy precursor of the compound of this invention.

Alternatively, an amide can be formed on the secondary amine function with an acylating agent

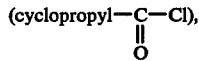

and then reduced to a tertiary amine function with LiAlH$_4$ or other similar reducing agent, to yield cis-dl-3a-(m-methoxyphenyl)-1-cyclopropylmethyl-1,2,3,3a,4,5,6,7,7a,8-decahydroisoquinoline. The compound can be readily dimethylated, as with 48% HBr in acetic acid to provide the compound of this invention.

An alternate and preferable procedure has been developed for the preparation of the cis-decahydrosioquinoline of this invention. In this procedure, 2-(m-methoxyphenyl)-cycloheptanone, a known compound, is alkylated with bromacetic ester in the presence of sodamide to yield 2-ethoxycarbonylmethyl-2-(m-methoxyphenyl)cycloheptanone. Formylation with ethyl formate yields the 7-formyl derivative of 2-ethoxycarbonylmethyl-2-(m-methoxyphenyl)cycloheptanone. Reaction of this formyl compound with p-tosyl azide in the presence of diethylamine yields the corresponding 7-diaza compound. Irradiation of the diazaketone with ultraviolet light in a lower alkanol, for example, methanol, causes a rearrangement to take place. The product of this rearrangement, a cyclohexanecarboxylic acid derivative, is 2-(m-methoxyphenyl)-2-ethoxycarbonylmethylcyclohexanecarboxylic acid ester. Hydrolysis of the diester with base yields a 1,3-diacid; i.e., 2-(m-methoxyphenyl)-2-carboxymethylcyclohexanecarboxylic acid. The diacid is obtained as a mixture of geometric isomers, cis and trans, in that both carboxyl groups can be on the same side of the cyclohexane ring (cis) or on opposite sides of the cyclohexane ring (trans). (Ordinarily, the cis and trans designation is based upon the orientation of the phenyl and hydrogen groups attached to the same carbons as the carboxylic acid and the carboxymethyl group). Two fractions, are the cis and the other the trans isomer, of the dicarboxylic acid are isolated and both subjected to treatment with acetyl chloride or other dehydrating agent to form the corresponding anhydride, named systematically as cis (or trans)-3,4,4a,5,6,7,8,8a-octahydro-1,3-dioxo-1H-2-benzopyran (VII). Reaction of the cis anhydride only with cyclopropylmethylamine yields the corresponding dioxodecahydroisoquinoline (VIII, cis-dl-1,2,3,3a,4,5,6,7,7a,8-decahydro-3a-(m-methoxyphenyl)-1,3-dioxo-1-methylisiquinoline. Reduction of the dioxo derivative with lithium aluminum hydride in THF or other suitable solvent yields the corresponding decahydroisoquinoline itself (IX) named, in the case where the N-substituent is cyclopropylmethyl, as cis-dl-1-cyclopropylmethoxy-3a-(m-methoxyphenyl)-1,2,3,3a,4,5,6,7,7a,8-decahydroisoquinoline. The methoxy derivative is converted to the corresponding m-hydroxyphenyl derivative by demethylation employing, for example, 48 percent hydrogen bromide in acetic acid as the demethylating reagent. The product of this reaction (X) is, cis-dl-1-methyl-3a-(m-hydroxyphenyl)-1,2,3,3a,4,5,6,7,7a,8-decahydroisoquinoline. The above synthetic procedure is more fully set forth in Reaction Sequence III which follows.

Alternatively, the trans anhydride (VII) can react with cyclopropylmethylamine to yield a half-amide which can in turn be ring-closed by treatment with acetic anhydride to yield the trans analogus of VIII. This compound can then be eplimerized as by treatment with 30% KOH in dioxane to VIII itselt.
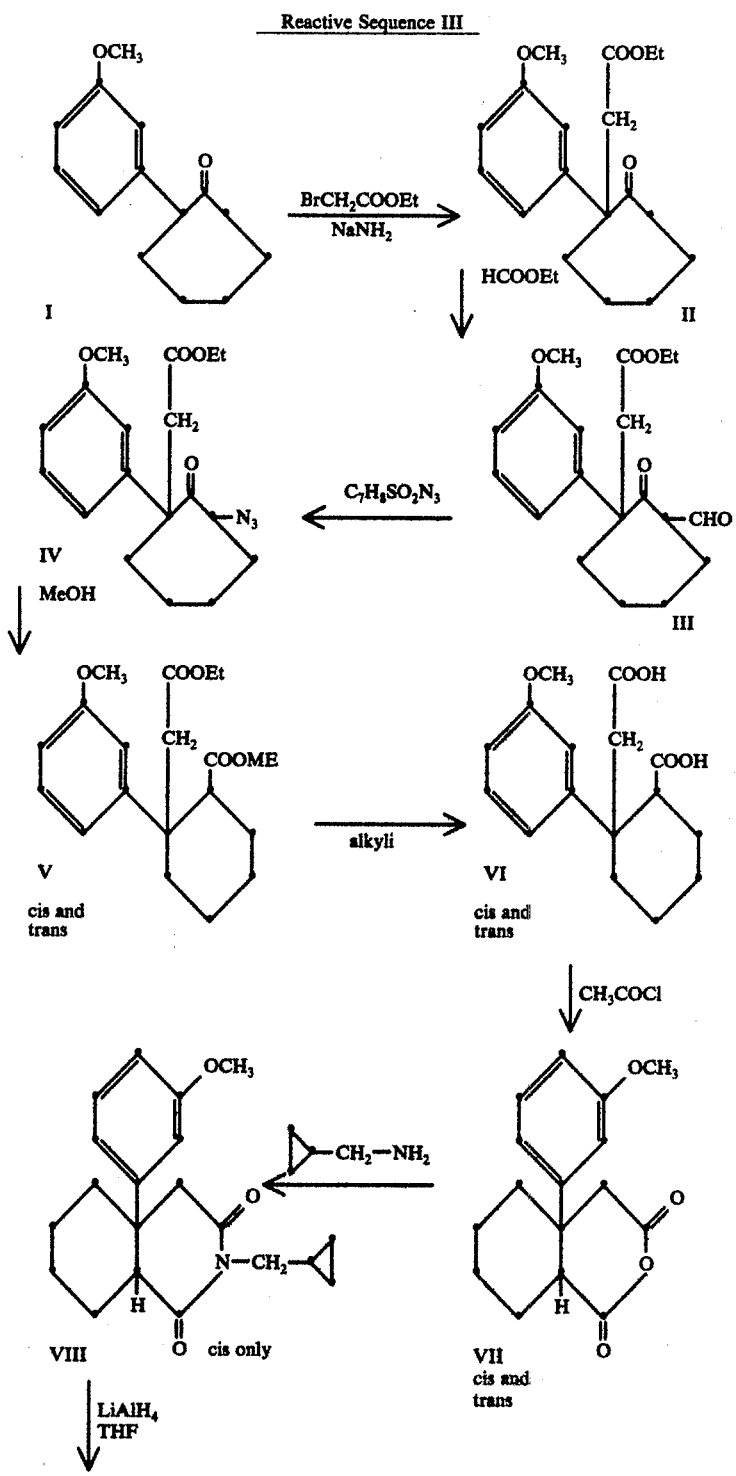
Reactive Sequence III

Reactive Sequence III

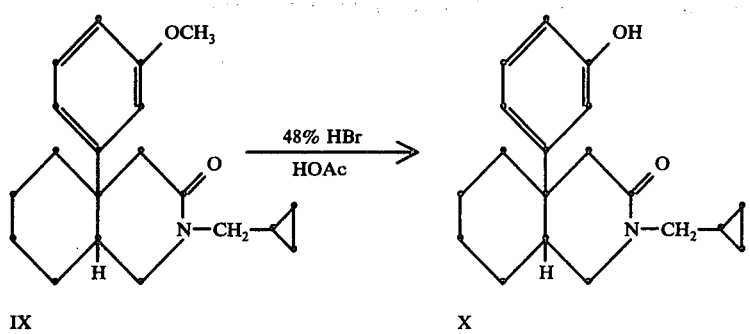

Alternatively, the cis-decahydroisoquinoline of this invention, either compound IX or compound X from Reaction Sequence III synthesized by preparing cis-dl-1-methyl-3a-(m-methoxyphenyl)-1,2,3,3a,4,5,6,7,7a,8-decahydroisoquinoline (VIII above with methyl in place of cyclopropylmethyl) by using methylamine in place of cyclopropylmethylamine. This compound or its O-demethyl analog can be N-demethylated by the procedure outlined for compound VIa from Reaction Sequence II using phenyl chloroformate. The resulting secondary amine is then acylated with cyclopropylcarboxyl chloride or other acylating agent to form an amide. Reduction of the amide with LiAlH₄ yields either the compound of this invention, cis-dl-1-cyclopropylmethyl-3a-(m-hydroxyphenyl)-1,2,3,3a,4,5,6,7,7a,8-decahydroisoquinoline or its m-methoxyphenyl analogue which can be converted to the m-hydroxy compound of this invention with 48 percent HBr in acetic acid or the like.

A third procedure for preparing the secondary amine, cis-dl-3a-(m-methoxyphenyl)-1,2,3,3a,4,5,6,7,7a,8-decahydroisoquinoline, has been provided whereby benzylamine is substituted for cyclopropylmethylamine in the preparation of the dioxo decahydroisoquinoline (Compound VIII) of Reaction Sequence III. Reduction of the dioxo compound yields an N-benzyl cis-dl-decahydroisoquinoline (compound IX). Debenzylation with Raney nickel yields the desired secondary amine which can be acylated with cyclopropylcarboxyl chloride to yield an amide, reduction of which to the N-cyclopropylmethyl derivative followed by O-demethylation yields the compound of this invention.

A second alternative procedure exists for the preparation of the cis derivative of this invention. The compound disclosed on page 9, Example 1, part B, of Belgian patent 802,557, called by them 4a-phenyl-1,3-diketo-1,2,3,4,4a,5,6,7-octahydroisoquinoline, if reduced directly with palladium-on-carbon yields the cis isomer only. The reaction can be applied to related compounds. Thus, for example, 3a-(m-methoxyphenyl)-2,8-dioxo-1,2,3,3a,4,5,6,8-octahydroisoquinoline upon reduction with palladium-on-carbon yields cis-dl-3a-(m-methoxyphenyl)-1,2,3,3a,4,5,6,7,7a,8-decahydroisoquinoline substantially exclusively.

The above procedure is illustrated in Reaction Sequence IV which follows.

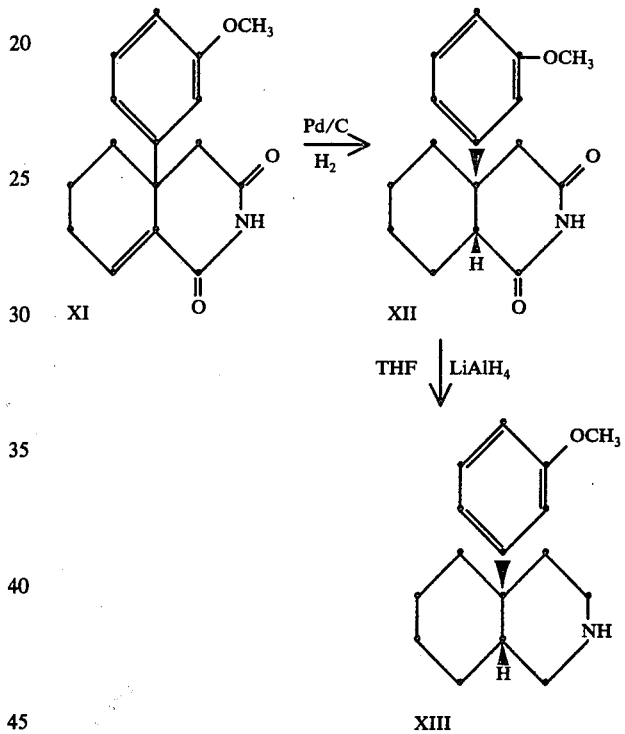

Compound XIII from Reaction Sequence IV is, of course, the same secondary amine discussed above and can be acylated with cyclopropylcarboxyl chloride to yield an amide, the amide reduced to give an N-cyclopropylmethyl compound which is O-demethylated to yield the compound of this invention.

This invention is further illustrated by the following specific examples.

EXAMPLE 1

A mixture was prepared containing 368 g. of 2-(β-cyanoethyl)-2-(m-methoxyphenyl)cyclohexanone, 2000 ml. of glacial acetic acid, 850 ml. of 12 N aqueous hydrochloric acid and 850 ml. of water. The mixture was refluxed for about 19 hours and then cooled to room temperature. Sufficient ice and water were added to make a volume of about 11 liters. The resulting mixture was stirred for about 30 minutes at which point a precipitate comprising 2-(β-carboxyethyl)-2-(m-methoxyphenyl)cyclohexanone formed. The supernate was removed by centrifugation, and the precipitate collected. The precipitate was thoroughly washed with water and then dried to yield about 280 g. of 2-(β-carboxyethyl)2-(m-methoxyphenyl)cyclohexanone melting at about 143°–4° C. after recrystallization from water.

About 225 g. of 2-(β-carboxyethyl)-2-(m-methoxyphenyl)cyclohexanone were mixed with 125 g. of triethylamine and about 20 g. of sodium sulfate. A solution of 99 g. of ethyl chloroformate in 3250 ml. of anhydrous ether was added in dropwise fashion, thus converting the carboxyethyl group to an acid anhydride. The reaction mixture was stirred for about 1 hour at about 0° C. at which point 89 g. of sodium azide in 350 ml. of water were added in dropwise fashion. After the addition had been completed, the reaction mixture was stirred for an additional two hours at 0° C. The ether layer was then separated. 2-(β-Azidoformylethyl)-2-(m-methoxyphenyl)cyclohexanone formed in the above reaction was isolated as an oil by evaporation of the ether in vacuo. The residual oil was dissolved in 3.5 l. of benzene, and the solution heated at refluxing temperature for about 1.5 hours. The benzene was removed by evaporation in vacuo. By this procedure the azidoformyl group was rearranged under Curtius conditions to yield the corresponding isocyanate. The benzene was removed by evaporation in vacuo. The isocyanate remaining as a residue was next hydrolyzed to the cyclic imine by heating overnight in a mixture containing 1200 ml. of water, 1200 ml. of glacial acetic acid and 1200 ml. of 12N aqueous hydrochloric acid. The hydrolysis mixture was cooled and then made strongly basic with 50 percent aqueous sodium hydroxide. 3a-(m-methoxyphenyl)-2,3,3a,4,5,6,7-heptahydroindole thus produced was extracted into ether, and the ether layer separated, washed with water and dried. Evaporation of the ether layer to dryness yielded 153.2 g. of 3a-(m-methoxyphenyl)-2,3,3a,4,5,6,7-heptahydroindole, distilling at about 140° C. at 0.07 mm/g. (For comparison, see Langlois et al., *Tetrahedron*, 27, 5641 (1971) compound 10 and page 5647, table 4, compound 42).

About 341 g. of 3a-(m-methoxyphenyl)-2,3,3a,4,5,6,7-heptahydroindole were dissolved in 600 ml. of methyl ethyl ketone. 184 g. of dimethyl sulfate were added to this solution in dropwise fashion. The reaction mixture was heated at refluxing temperature for one hour. 1100 ml. of water were then added over a one-half hour period and the reaction mixture refluxed for another three hours. The reaction mixture was made strongly basic with 50 percent aqueous sodium hydroxide with external cooling provided. 1-Methyl-3a-(m-methoxyphenyl)-2,3,3a,4,5,6,7-heptahydroindole formed in the above reaction, being insoluble in the alkaline layer, separated and was extracted into ether. The ether extract was separated, washed with water and dried. Evaporation of the ether in vacuo left a residual oil comprising 1-methyl-3a-(m-methoxyphenyl)-2,3,3a,4,5,6,7-heptahydroindole boiling at about 144° C. at 0.4 mm/Hg; yield = 325.4 g.

325.4 g. of 1-methyl-3a-(m-methoxyphenyl)-2,3,3a,4,5,6,7-heptahydroindole were dissolved in 2500 ml. of ether. A 50 percent mixture of 50 percent fluoboric acid and anhydrous ethanol was added in dropwise fashion with stirring until the solution was acid to congo red. The ether layer was separated by syphoning. The aqueous layer, which contained 1-methyl-3a-(m-methoxyphenyl)-2,3,3a,4,5,6,7-heptahydroindolinium fluoborate formed in the above reaction, was allowed to stand while the fluoborate salt slowly crystallized. The salt was collected by filtration, and the filter cake washed with ether. The filter cake was then triturated with an anhydrous ethanol-ether solvent mixture. The solvent was separated by filtration, and the filter cake was dried. Yield of the fluoroborate salt was about 392 g.

A solution of 55 g. of 1-methyl-3a-(m-methoxyphenyl)-2,3,3a,4,5,6,7-heptahydroindolinium fluoborate in 500 ml. of methylene chloride was cooled to about 0° C. A solution of diazomethane prepared from 103 g. of N-methyl-N-nitroso-p-toluenesulfonamide in ether was added over a five-hour period. The reaction mixture was allowed to warm to room temperature and was stirred overnight. The supernate was separated from the precipitated oil comprising the fluoborate salt of the corresponding aziridinium compound, 1-azonia-1-methyl-4-(m-methoxyphenyl)tricyclo[4,2,1,0$^{2-8a}$] decane. The oily residue was triturated with three 1000 ml. portions of ether, and the ether washes were discarded. The residual oil was transferred to a 500 ml. round-bottom flask and heated at atmospheric pressure for about an hour at 200° C., thus forming 1-methyl-3a-(m-methoxyphenyl)-1,2,3,3a,4,5,6,7-octahydroisoquinoline, which compound was dissolved in anhydrous ethanol, and the ethanol solution treated with an excess of 50 percent aqueous sodium hydroxide and water. The octahydroisoquinoline, being insoluble in the alkaline solution, separated and was extracted into ether. The ether extract was separated and dried, and the ether removed therefrom by evaporation in vacuo. 1-methyl-3a-(m-methoxyphenyl)-1,2,3,3a,4,5,6,7-octahydroisoquinoline thus prepared distilled at about 168° C. at 0.5 mm/hg.

A mixture was prepared containing about 163 g. of 1-methyl-3a-(m-methoxyphenyl)-1,2,3,3a,4,5,6,7-octahydroisoquinoline, 90 g. of sodium borohydride and 4500 ml. of tetrahydrofuran was cooled to about 5° C. 1630 ml. of acetic acid were added in dropwise fashion while maintaining the temperature with mild heating. The mixture was refluxed for one hour, and was then made strongly basic with about 3 liters of 25 percent aqueous sodium hydroxide. The tetrahydrofuran layers where combined and evaporated to dryness in vacuo. The resulting residue, comprising trans-dl-1-methyl-3a-(m-methoxyphenyl)-1,2,3,3a,4,5,6,7,7a,8-decahydroisoquinoline with a small amount of the cis-dl racemate formed in the above reaction, was dissolved in about 3.5 l. of ether, and the ethereal layer washed with three 2 l. portions of water. The ether layer was dried, and the ether removed therefrom by evaporation to dryness in vacuo. The yield of the decahydroisoquinoline was 162.3 g.

The trans racemate was purified via the picrate salt (m.p. = 161°–2° C.) which was converted back to the free base by refluxing the salt with saturated lithium hydroxide at the ratio 30 g. of picrate to 1000 ml. of saturated aqueous lithium hydroxide solution. Extraction of the free base into benzene followed by distillation of the base yield trans-dl-1-methyl-3a-(m-methoxyphenyl)-1,2,3,3a,4,5,6,7,7a,8-decahydroisoquinoline boiling in the range 145°–79° C. at 0.1 mm/Hg. The cis-dl racemate did not form an insoluble picrate salt and remained in the filtrate.

The 1-methyl group was cleaved by dissolving 8 g. of trans-dl-1-methyl-3a-(m-methoxyphenyl)-1,2,3,3a,4,5,6,7,7a,8-decahydroisoquinoline in 64 ml. of methylene chloride and adding thereto a solution of 5.6 g. of phenyl chloroformate in 16 ml. of methylene chloride. The resulting mixture was refluxed for about two hours, and allowed to stand overnight. The solvents were then evaporated in vacuo. 100 ml. of 5 percent aqueous sodium hydroxide were added, and the resulting mixture stirred with warming for about 15 minutes. 1-Phenylcarboxy-3a-(m-methoxyphenyl)-1,2,3,3a,4,5,6,7,7a,8-decahydroisoquinoline formed in the above reaction, being insoluble in the basic layer, separated and was extracted into ether. The ether extract was separated and washed with water. The ether extract was in turn extracted with 250 ml. of 10 percent aqueous hydrochloric acid followed by 250 ml. of water to remove any unreacted N-methyldecahydroisoquinoline. The ether layer was separated, dried, and the ether removed by evaporation. The residue was refluxed for 66 hours in 240 ml. of anhydrous ethanol and 50 ml. of 50 percent aqueous potassium hydroxide. The volatile constituents were removed in vacuo, and the resulting concentrate extracted with ether. The ether extract was separated and dried. Evaporation of the ether left a residue comprising 1-phenylcarboxy-3a-(m-methoxyphenyl)-1,2,3,3a,4,5,6,7,7a,8-decahydroisoquinoline was dissolved in 250 ml. of 10 percent aqueous hydrochloric acid. The acid layer was washed with ether, and the ether wash was discarded. The aqueous layer was made strongly basic with 50 percent sodium hydroxide, and trans-dl-3a-(m-methoxyphenyl)-1,2,3,3a,4,5,6,7,7a,8-decahydroisoquinoline thus formed was extracted into ether. The ether layer was separated, dried and the ether removed therefrom by evaporation. Distillation of the resulting residue yielded 5.5 g. of trans-dl-3a-(m-methoxyphenyl)-1,2,3,3a,4,5,6,7,7a,8-decahydroisoquinoline boiling at about 148° C. at 0.2 mm/Hg.

Trans-dl-3a-(m-methoxyphenyl)-1,2,3,3a,4,5,6,7,7a,8-decahydroisoquinoline was converted to the corresponding 3a-(m-hydroxyphenyl) derivative by treatment with 50 percent HBr in 50 percent aqueous acetic acid. In this procedure, 5.2 g. of freshly distilled 3a-(m-methoxyphenyl)-1,2,3,3a,4,5,6,7,7a,8-decahydroisoquinoline were dissolved in 40 ml. of 50 percent aqueous hydrobromic acid and 40 ml. of 50 percent aqueous acetic acid. The resulting mixture was refluxed for 18 hours. The reaction mixture was cooled, diluted with about 250 ml. of water and the pH thereof adjusted to about 10.4 with 50 percent aqueous sodium hydroxide. The reaction mixture was treated with a 3:1 n-butanol-benzene solvent system. Trans-dl-3a-(m-hydroxyphenyl)-1,2,3,3a,4,5,6,7,7a,8-decahydroisoquinoline, being insoluble in the alkaline layer, passed into the organic layer. The organic layer was separated and dried, and the solvents removed therefrom by evaporation in vacuo. 5 g. of trans-dl-3a-(m-hydroxyphenyl)-1,2,3,3a,4,5,6,7,7a,8-decahydroisoquinoline were obtained which melted at about 212°-214° C. with decomposition after recrystallization from dimethylformamide.

Analysis Calc.: C, 76.67; H, 9.65; N, 6.39; Found: C. 76.88; H, 9.35; N, 6.24.

All of the above reactions are equally operative, starting with the N-methyl cis-dl racemate, to prepare, cis-dl-3a-(m-methoxyphenyl)-1,2,3,3a,4,5,6,7,7a,8-decahydroisoquinoline and its m-hydroxyphenyl analogue.

EXAMPLE 2

Ten grams of trans-dl-3a-(m-hydroxyphenyl)-1,2,3,3a,4,5,6,7,7a,8-decahydroisoquinoline and 11.7 ml. of triethylamine were dissolved in 170 ml. of dimethylformamide. 11.4 g. of cyclopropylcarboxyl chloride were added to this solution in dropwise fashion. The resulting mixture was heated in the range of 65°-80° C. for about two hours, was cooled, and was then poured into about 1000 ml. of water. Trans-dl-1-cyclopropylcarbonyl-3a-(m-hydroxyphenyl)-1,2,3,3a,4,5,6,7,7a,8-decahydroisoquinoline formed in the above reaction was extracted therefrom with three 1000 ml. portions of ether. The ether extracts were combined and the combined fractions washed with three 300 ml. portions of saturated aqueous sodium chloride followed by one 200 ml. water wash. The ether layer was separated and dried, and the ether removed therefrom by evaporation in vacuo. The dried residue was dissolved in 100 ml. of THF (tetrahydrofuran) and this solution added dropwise to a solution of 6.5 g. of lithium aluminumhydride in 300 ml. of THF. After the addition had been completed, the reaction mixture was heated to reflux for about four hours. Next, about 75 ml. of ethyl acetate were added to react with any excess lithium aluminumhydride present. Saturated ammonium tartrate was added to decompose inorganic salts present and to cause them to coagulate. The THF solution was then separated by decantation, and the residual salts washed with three 500 ml. portions of THF. The THF washes were combined with the original THF layer, and the solvent removed by evaporation to dryness in vacuo. The residual product comprising trans-dl-cyclopropylmethyl-3a-(m-hydroxyphenyl)-1,2,3,3a,4,5,6,7,7a,8-decahydroisoquinoline melted at about 164°-6° C. after recrystallization from ethyl acetate.

Analysis: Calc. for $C_{19}H_{27}NO$; C, 79.97; H, 9.54; N, 4.91; Found: C, 79.72; H, 9.63; N, 4.62.

The maleate salt was prepared from the free base: m.p. 146°-8° C.

Analysis: Calc. for $C_{23}H_{31}NO_5$; C, 68.80; H, 7.78; N, 3.49; Found: C, 68.52; H, 7.80; N, 3.68.

The above reactions can be adapted to the preparation of cis-dl-1-cyclopropylmethyl-3a-(m-hydroxyphenyl)-1,2,3,3a,4,5,6,7,7a,8-decahydroisoquinoline starting with cis-dl-3a-(m-hydroxyphenyl)-1,2,3,3a,4,5,6,7,7a,8-decahydroisoquinoline.

As previously stated, the compounds of this invention represented by formula I above contain two asymmetric centers, at 3a and 7a. Thus the compounds can exist as four diastereoisomers occuring as two racemic pairs, commonly designated as the cis-dl and the trans-dl racemates.

The preparation of optically-active isomers of compounds according to Structure I, are illustrated below.

EXAMPLE 3

Thirty six and two-tenths grams of trans-dl-1-methyl-3a-(m-methoxyphenyl)-1,2,3,3a,4,5,6,7,7a,8-decahydroisoquinoline and 23.4 g. of L(+)-mandelic acid were dissolved 100 ml. of isopropanol. The solvent was removed by evaporation and the residue recrystallized from 1000 ml. of water. The resulting precipitate weighing 21.1 g. was separated by filtration and recrystallized from a mixture of 28 percent acetone and 72 percent isopropyl ether. A sample of the mandelate salt was treated with an excess of 1N sodium hydroxide. Trans-l-(−)-1-methyl-3a-(m-methoxyphenyl)-1,2,3,3a,4,5,6,7,7a,8-decahydrolisoquinoline, being insoluble in the aqueous alkaline layer, separated and was extracted into ether. The ether extract was separated and the ether evaporated therefrom. The rotation of the residual free base was obtained by standard procedures. The recrystallization of the L(+)-mandelate salt above from 28 percent acetone-72 percent isopropyl ether continued until the samples of the trans-l-(−)-1-methyl-3a-(m- methoxyphenyl)-1,2,3,3a,4,5,6,7,7a,8-decahydrolisoquinoline showed a constant rotation after repeated recrystallization. Trans-1-(—)-1-methyl-3a-(m-methoxyphenyl)-1,2,3,3a,4,5,6,7,7a,8-decahydrolisoquinoline thus prepared had a rotation of $[\alpha]_{350}^{25°} = -48.1°$. L(+)-mandelate salt;

Analysis Calc.: C, 72.96; H, 8.08; N, 3.40; Found: C, 72.67; H, 8.21; N, 3.23.

The above procedure was repeated using D(—) mandelic acid in place of L(+)-mandelic acid in the above procedure. Trans-d(—)-1-methyl-3a-(m-methoxyphenyl)-1,2,3,3a,4,5,6,7,7a,8-decahydrolisoquinoline thus obtained had the following rotation: $[\alpha]_{350}^{25°} = +47.6°$.

Following the procedure of Example 1 both the trans-1-(+)- and trans-d(—)-1-methyl-3a-(m-methoxyphenyl)-1,2,3,3a,4,5,6,7,7a,8-decahydroisoquinoline isomers were N-demethylated and O-demethylated to yield respectively trans-1-(+) and trans-d(—)-3a-(m-hydroxyphenyl)-1,2,3,3a,4,5,6,7,7a,8-decahydroisoquinoline isomers. N-acylation of the individual isomers with cyclopropylcarbonyl chloride followed by reduction of the resulting amides with LiAlH₄ by the procedure of Example 2 yielded trans-1-(—)-1-cyclopropylmethyl-3a-(m-hydroxyphenyl)-1,2,3,3a,4,5,6,7,7a,8-decahydrolisoquinoline, maleate salt: m.p. 197.5°–109° C.: $[\alpha]_{350}^{25°} = -12.7$; $[\alpha]_d^{25°} = -3.8$.

Analysis Calc.: C, 68.80; H, 7.78; N, 3.48; Found: C, 68.70; H, 7.62; N, 3.31.

And trans-d(+)-1-cyclopropylmethyl-3a-(m-hydroxyphenyl)-1,2,3,3a,4,5,6,7,7a,8-decahydrolisoquinoline, maleate salt: m.p. 109.5°–110° C.; $[\alpha]_{350}^{25°} = +16.2$; $[\alpha]_d^{25°} = +5.9$.

Analysis Calc.: C, 68.80; H, 7.78; N, 3.49; Found: C, 68.56; H, 7.62; N, 3.26.

The optically active isomers of the cis-dl-series; i.e., cis-d(+)-1-cyclopropylmethyl-3a-(m-hydroxyphenyl)-1,2,3,3a,4,5,6,7,7a,8-decahydroisoquinoline, and cis-1-(—)-1-cyclopropylmethyl-3a-(m-hydroxyphenyl)-1,2,3,3a,4,5,6,7,7a,8-decahydroisoquinoline are prepared in an entirely analogous fashion from the cis-dl racemate.

EXAMPLE 4

Preparation of Salts

Salts of the free bases of this invention, other than the mandelate or maleate salts whose preparation is illustrated above, are prepared by dissolving the free base in ether and adding an equivalent of a suitable non-toxic acid, also in ether. The salts thus formed, as for example the sulfate and phosphate salts, are insoluble in ether and can be isolated by filtration. Alternatively, the amine base can be dissolved in ethanol and an equivalent of the acid added as an ethanolic solution. In this instance, since the salts thus formed are at least partially soluble in the reaction mixture, they are isolated by evaporation of the solvent in vacuo. Salts which can be formed by the above procedure include the hydrochloride, sulfate, hydrobromide, phosphate, hydrogen phosphate, dihydrogen phosphate, acetate, maleate, succinate, tartrate, citrate, benzoate, and p-toluene sulfonate salts of cis-dl-1-cyclopropylmethyl-3a-(m-hydroxyphenyl)-1,2,3,3a,4,5,6,7,7a,8-decahydroisoquinoline.

EXAMPLE 5

Preparation of 2-m-Methoxyphenyl)-2-Ethoxycarbonylmethylcycloheptanone

A solution was prepared containing 181 g. of 2-(m-methoxyphenyl)cycloheptanone (prepared by the procedure of *Organic Syntheses*, Collective Volume IV, page 780) in 200 ml. of benzene. This solution was added in dropwise fashion to a stirred refluxing suspension of 43 g. of sodamide in 1500 ml. of benzene. After the addition had been completed, the reaction mixture was refluxed for an additional 2.5 hours, and was then chilled to about 0° C. A solution of 136 g. of ethyl bromoacetate in 200 ml. of benzene was added in dropwise fashion. The resulting mixture was stirred overnight at ambient temperature, and was then poured into cold water. The benzene layer was separated and the aqueous layer extracted twice with equal volumes of benzene. The benzene layer and extracts were combined, washed with water until the washes were neutral to litmus and then dried. Evaporation of the solvent yielded 207 g. of a residue comprising 2-(m-methoxyphenyl)-2-ethoxycarbonylmethylcycloheptanone. The compound was purified by distillation, distilling at about 160° C. at a pressure of 0.1 mm./Hg.

Analysis Calcd.: C, 72.13; H, 7.65; Found: C, 72.47; H, 7.88.

EXAMPLE 6

Preparation of 2-(m-Methoxyphenyl)-2-Ethoxycarbonylmethyl-7-Formylcycloheptanone A mixture was prepared containing 313 g. of 2-(m-methoxyphenyl)-2-ethoxycarbonylmethyl-cycloheptanone, 2 liters of ether, 332.9 g. of sodium and 115.7 g. of ethyl formate. The reaction mixture was stirred at ambient temperature for 5 days and then poured onto an ice-water mixture. The ether layer was separated and saved for recovery of starting material. The aqueous layer was acidified with cold 10 percent aqueous hydrochloric acid and the resulting acidic layer extracted with an equal volume of ether. The ether extract was separated, washed three times with a saturated aqueous sodium chloride solution and then dried. Evaporation of the solvent yielded 243 g. of 2-m-methoxyphenyl)-2-ethoxycarbonylmethyl-7-formylcycloheptanone. Molecular ion by mass spectrograph 332.

Analysis Calcd: C, 68.66; H, 7.28; Found: C, 68.37; H, 7.56.

EXAMPLE 7

Preparation of 2-(m-Methoxyphenyl)-2-Ethoxycarbonylmethyl-7-Diazacycloheptanone

A solution was prepared containing 243 g. of 2-(m-methoxyphenyl)-2-ethoxycarbonylmethyl-7-formylcycloheptanone in 400 ml. of ether. A solution of 106 g. of diethylamine in 400 ml. of ether was added to the cycloheptanone derivative solution in dropwise fashion. The reaction mixture was stirred at ambient temperature for about 2 hours and then cooled to about 5° C. Next, a solution of 146 g. of p-toluenesulfonylazide in 400 ml. of ether was added in dropwise fashion. The reaction mixture was allowed to warm to ambient temperature and was stirred at that temperature for an additional five hours. The reaction mixture was then washed with water, and the ether layer separated and dried. Evaporation of the solvent under reduced pressure yielded 283 g. of 2-(m-methoxyphenyl)-2-ethoxycarbonylmethyl-7-diazacycloheptanone as an oil. Infrared spectrum of the oil showed a band at about 2075 cm$^{-1}$ characteristic of the diazaketone grouping.

EXAMPLE 8

Preparation of Methyl 2-(m-Methoxyphenyl)-2-Ethoxycarbonylmethylcyclohexanecarboxylate A solution was prepared from 283 g. of 2-(m-methoxyphenyl)-2-ethoxycarbonylmethyl-7-diazacycloheptanone in 1300 ml. of methanol. The solution was placed in a quartz vessel, the atmosphere flushed with nitrogen and a positive nitrogen pressure applied. The reaction mixture was then irradiated with ultraviolet light at 3,000 Å from a quartz lamp. Irradiation was continued until an aliquot sample taken from the reaction mixture gave no IR peak at 2075 cm$^{-1}$, indicative that there was no remaining diaza compound in solution. The product of the reaction, 2-(m-methoxyphenyl)-2-ethoxycarbonylmethylcyclohexanecarboxylate, produced by photolysis of the diazaketone was recovered as an oil weighing 272 g. upon evaporation of the solvent. The solvent was redissolved in ether and washed with aqueous sodium bicarbonate solution followed by water. The ether solution was separated, dried, and distilled. Upon distillation, fractions boiling in the range 190°–220° C. at 0.1 mm./Hg. and 220°–227° C. at 0.1 mm./Hg. were collected (total weight, 177 g.). The combined fractions were indicated by gas chromatography to contain 77 percent of the desired product. The combined products were therefore, redistilled through a short path vigreaux column to yield 2-(m-methoxyphenyl)-2-ethoxycarbonylmethylcyclohexanecarboxylate boiling at 178° C. at 0.05 mm./Hg. Yield: 116 g.

Analysis Calcd: C, 68.24; H, 7.84; Found: C, 68.15; H, 7.57.

EXAMPLE 9

Preparation of 2-(m-Methoxyphenyl)-2-Carboxymethylcyclohexanecarboxylic Acid 67 g. of methyl 2-(m-methoxyphenyl)-2-ethoxycarbonylmethylcyclohexanecarboxylate were mixed with 700 ml. of 5 percent aqueous potassium hydroxide in 900 ml. of dioxane. The reaction mixture was heated at refluxing temperature overnight and then cooled. Removal of the solvent in vacuo left an oily residue which was dissolved in water and the water layer extracted with ether. The ether layer was discarded. The aqueous layer was acidified with 10 percent aqueous hydrochloric acid. 2-(m-Methoxyphenyl)-2-carboxymethylcyclohexanecarboxylic acid being insoluble in the acidic aqueous layer separated and was extracted into ether. The ether layer was separated, washed with water and dried. Evaporation of the ether in vacuo left a semi-solid residue which crystallized in part upon addition of ether. About 19.2 g. of trans-dl-2-(m-methoxyphenyl)-2-carboxymethylcyclohexanecarboxylic acid were obtained as a crystalline precipitate. Evaporation of ether from the filtrate yielded 35 g. of cis-dl-2-(m-methoxyphenyl)-2-carboxymethylcyclohexanecarboxylic acid.

Analysis Calcd.: C, 65.74; H, 6.90; Found: C, 65.95; H, 6.66.

The above assignments of configuration (cis and trans) were based upon the ability of the particular isomer to form an imide by the reaction of Example 10 below.

EXAMPLE 10

Preparation of Trans-dl-3,4,4a,5,6,7,8,8a-Octahydro-1,3-Dioxo-1H-2-Benzopyran A solution of 35 g. of trans-2-(m-methoxyphenyl)-2-carboxymethylcyclohexanecarboxylic acid in 300 ml. of acetyl chloride was stirred at reflux temperature for about 4 hours. The reaction mixture was cooled, excess acetyl chloride removed by evaporation in vacuo and the residue comprising trans-dl-3,4,4a,5,6,7,8,8a,-octahydro-1,3-dioxo-1H-2-benzopyran was purified by distillation; boiling point = 210°–240° C. at 0.2 mm./Hg.

Analysis Calcd.: C, 70.06; H, 6.61; Found: C, 69.80; H, 6.41.

EXAMPLE 11

Preparation of Cis-dl-1,2,3,3a,4,5,6,7,7a,8-Decahydro-3a-(m-Methoxyphenyl)-1-Benzyl-2,8-Dioxoisoquinoline A solution of 19.5 g. of cis-dl-3,4,4a,5,6,7,8,8a-octahydro-1,3-dioxo-1H-2-benzopyran in 450 ml. of toluene was prepared and added dropwise to a solution of 7.6 g. of benzylamine in 450 ml. of toluene. The reaction mixture was heated at refluxing temperature for two hours after the addition had been completed, was then cooled and the solvent removed therefrom by evaporation in vacuo. Treatment of the resulting residue with 1N aqueous sodium hydroxide dissolved the N-benzyl half-amide of trans-dl-2-(m-methoxyphenyl)-2-carboxymethyl cyclohexanecarboxylic acid formed in the above reaction. The alkaline solution was washed with ether, and the ether wash separated and discarded. The alkaline layer was then made acidic with 10 percent aqueous hydrochloric acid. The half-amide, being insoluble in the acidic solution separated and was extracted into ether. The ether solution was separated, dried, and the ether evaporated therefrom. The half-amide was obtained in 26 g. yield as a gummy oil.

The half-amide thus obtained was mixed with 11.3 g. of sodium acetate and 150 ml. of acetic anhydride. The reaction mixture was heated to about 100° C. for about 30 minutes and then cooled. The reaction mixture was then poured into an ice-water mixture. Trans-dl-1-benzyl-3a-(m-methoxyphenyl)-1,2,3,3a,4,5,6,7,7a,8-decahydro-2,8-dioxoisoquinoline obtained in the above reaction being water insoluble separated and was extracted with ether. The ether extract was separated, washed with water, and dried. Evaporation of the solvent yielded a viscous oil. The oil was dissolved in ether and the ether solution washed with 1N aqueous sodium hydroxide. The ether layer was then washed with water until the water washes were neutral to litmus. The ether layer was then separated, dried and the ether removed therefrom in vacuo yielding 20 g. of a semi-solid mass comprising trans-dl-1-benzyl-3a-(m-methoxyphenyl)-1,2,3,3a,4,5,6,7,7a,8-decahydro-2,8-dioxoisoquinoline.

11 g. of the compound thus obtained was mixed with 250 ml. of 30 percent aqueous potassium hydroxide and 400 ml. of p-dioxane. The reaction mixture was heated to refluxing temperature for 30 minutes and then cooled. The dioxane was removed by evaporation. The oily residue comprising cis-dl-1-benzyl-3a-(m-methoxyphenyl)-1,2,3,3a,4,5,6,7,7a,8-decahydro-2,8-dioxoisoquinoline obtained in the above racemization was dissolved in ether. The ether layer was washed with water until the water extracts were neutral to litmus. The ether extract was then dried and the solvent removed by evaporation in vacuo, yielding 16 g. of the cis compound as a residue.

A suspension of 3.3 g. of lithium aluminumhydride was prepared in 300 ml. of tetrahydro-furan. 16 g. of cis-dl-1-benzyl-3a-(m-methoxyphenyl)-1,2,3,3a,4,5,6,7,7a,8-decahydro-2,8-dioxoisoquinoline were dissolved in 233 ml. of anhydrous tetrahydrofuran and the solution added in dropwise fashion to the lithium aluminumhydride suspension. The resulting reaction mixture was heated for 16 hours at reflux temperature and then cooled. Excess lithium aluminumhydride was destroyed in the usual fashion by the addition of ethyl acetate. Sufficient aqueous ammonium chloride solution was then added in dropwise fashion to precipitate the inorganic salts. The liquid phase was decanted from these salts, and the ether removed therefrom by evaporation in vacuo. The residue comprising cis-dl-1-benzyl-3a-(m-methoxyphenyl)-1,2,3,3a,4,5,6,7,7a,8-decahydroisoquinoline formed in the above reduction was dissolved in ether, and the ether solution washed with water until neutral. The ether solution was then dried, and the ether evaporated therefrom yielding 14 g. of an oil as a residue. The oil was dissolved in 470 ml. of anhydrous ethanol to which was added 14 g. of a 5 percent palladium-on-carbon suspension. The mixture was placed in a low-pressure hydrogenation aparatus and hydrogenated at 60° C. for 45 hours at a hydrogen pressure of 60 psi. When the uptake of hydrogen showed the reaction to be substantially complete, the catalyst was separated by filtration and the filtrate evaporated to dryness. The residue, comprising cis-dl-3a-(m-methoxyphenyl)-1,2,3,3a,4,5,6,7,7a,8-decahydroisoquinoline, was dissolved in ether and the ether layer extracted with cold dilute hydrochloric acid. The secondary amine base was soluble in the acidic layer which was separated. The separated acidic layer was then made basic and the amine base, being insoluble in alkali, separated and was extracted into ether. The ether extract was separated, washed with water until the washes were neutral and then dried. Evaporation of the solvent yielded about 4.5 g. of an oil which was shown to contain approximately 84 percent of cis-dl-3a-(m-methoxyphenyl)-1,2,3,3a,4,5,6,7,7a,8-decahydroisoquinoline and 15 percent of the trans isomer.

Next 4.3 g. of the mixture was mixed with 30 ml. of 48 percent aqueous hydrobromic acid and 30 ml. of glacial acetic acid. The reaction mixture was heated to refluxing temperature for 15 hours and then cooled. The reaction mixture was then poured into 300 ml. of crushed ice. Sufficient 50 percent aqueous sodium hydroxide was added to bring the pH of the solution to about 11. The alkaline layer was next twice extracted with 200 ml. portions of a 3:1 n-butanolbenzene solvent mixture. The extracts were combined and washed successively with water, saturated aqueous sodium chloride solution, and again water. The organic layer was dried and the solvents removed by evaporation leaving an oily residue containg cis-dl-3a-(m-hydroxyphenyl)-1,2,3,3a,4,5,6,7,7a,8-decahydroisoquinoline. The oil was dissolved in 250 ml. of boiling ethyl acetate. Chilling of the solution yielded crystalline material melting at 190°–194° C. weighing about 1.7 g. The crystalline solids were mixed with 1.7 g. of potassium carbonate, 75 ml. of methanol, and 9 ml. of water. The mixture was chilled to about 0° C. and 1.7 g. of cyclopropylcarboxyl chloride added thereto in dropwise fashion. The reaction mixture was stirred for one hour in the range −5° C. to 0° C. and then for one hour at ambient temperature. Volatile constituents were removed by evaporation in vacuo. The resulting residue containing cis-dl-1-cyclopropylcarbonyl-3a-(m-hydroxyphenyl)-1,2,3,3a,4,5,6,7,7a,8-decahydroisoquinoline formed in the above reaction was extracted into ether. The ether extract was washed with 5 percent aqueous sodium bicarbonate, with 10 percent hydrochloric acid and with water til neutral and was then dried. Evaporation of the ether left as a residue purified cyclopropylcarbonyl amide. The amide was dissolved in anhydrous THF and added to a solution of 2 g. of lithium aluminum hydride in 100 ml. of anhydrous THF. The resulting mixture was heated at reflux for 4 hours and then cooled. Excess lithium aluminum hydride was destroyed by the addition of ethyl acetate and sufficient ammonium chloride was added to precipitate inorganic salts present. The tetrahydrofuran layer was separated by decantation from the salts and the THF removed therefrom by evaporation. Cis-dl-1-cyclopropylmethyl-3a-(m-hydroxyphenyl)-1,2,3,3a,4,5,6,7,7a,8-decahydroisoquinoline formed in the above reduction was purified by standard procedures. The purified compound was dissolved in ether and gaseous HCl bubbled therein to precipitate a hydrochloric salt. About 2.2 g. of hydrochloride were obtained and were separated by filtration. The filtered solid was triturated with refluxing ethyl acetate for about 30 minutes. The solution was then cooled and the solids separated by filtration. Cis-dl-1-cyclopropylmethyl-3a-(m-hydroxyphenyl)-1,2,3,3a,4,5,6,7,7a,8-decahydroisoquinoline hydrochloride thus obtained melted at 220°–2° C.

Analysis Calc.: C, 70.90; H, 8.77; N, 4.53; Found: C, 70.69; H, 8.53; n, 4.41.

As previously stated, the compound of this invention has both opiate-agonist and opiate-antagonist properties. While the compound is capable of producing analgesia in mammals, the added characteristc of being simultaneously an opiate-antagonist and agonist greatly decreases the physical dependence (addiction) liability of the particular drug. It might be said that the opiate-antagonist activity of the compounds of this invention acts as a built-in safety device tending to mitigate any physical dependence-inducing (addictive) properties of the drug caused by its opiate-like analgesic action.

The compound of this invention demonstrates its analgesic activity in the mouse-writhing test and in the rat tail jerk assay, both standard pharmacological assays for analgesic action. For example, in the mouse writhing test, the compound of this invention has demonstrated activity in inhibiting writhing in mice induced by the intraperitoneal injection of acetic acid.

The I.D.$_{50}$ dose which inhibits 50% of the writhings was found to be 5 mg/kg S.C. and 50 mg/kg orally.

The compound of this invention is also active in the rat tail jerk assay, another standard pharmacologic test for analgesic activity of the opiate-type. Such activity is manifested as an increase in the reaction time of the animal in removing (jerking) its tail from a nearby heat stimulus (a resistance wire) after drug administration over control time (no drug administered).

The minnimal effective analgesic dose as determined by this procedure was found to be 2 mg./kg. S.C. and 20 mg/kg orally.

The ability of the compound of this invention to antagonize the action of morphine, an opiate, is shown by the following modification of the aforementioned rat tail jerk assay: The standard assay procedure is used with the exception that a 7 amps. current is used instead of a 6 amps. current in the hot wire to decrease the measurable agonist effects of the antagonist. The drug under test is then administered to groups of rats at different dose levels at different times prior to test, with a 5 mg./kg. dose of morphine invariably being administered 10 minutes prior to test. Positive evidence of antagonism is a decreased reaction time over the reaction time increase to be expected from the morphine. Suggestive evidence of antagonism is the finding of a reaction time less than that to be expected from the morphine dose added to the effect of the analgesic under test. cis-dl-1-Cyclopropylmethyl-3a-(m-hydroxyphenyl)-1,2,3,3a,4,5,6,7,7a,8-decahydroisoquinoline hydrochloride at a 1 or 2 mg./kg. S.C. dose administered 30 minutes prior to test reduced the analgesic response to 5 mg./kg. of morphine administered 10 minutes prior to test.

The compound of this invention can be employed to produce analgesia in mammals by administration by either the parenteral or oral route at a 10–100 mg. dose level. For oral dosage, a suitable quantity of a pharmceutically-acceptable salt of a base according to formula I, formed with a non-toxic acid, is mixed with starch or other excipient, and the mixture placed in telescoping gelatin capsules each containing an analgesic dose. Similarly, the salt can be mixed with starch, a binder, and a lubricant, and the mixture compressed into tablets each containing a standard analgesic dose. The tablets may be scored if lower or divided dosages are to be used. With parenteral administration, the intramuscular or subcutaneous routes are preferred. For this purpose, aqueous solutions or suspensions are employed using a pharmaceutically-acceptable salt of the amine base of formula 1. In general, modes of administration and pharmaceutical forms found useful in the past for morphine, codeine, methadon, meperidine and other opiate-like analgesics can be adopted by those skilled in the art for the compounds of this invention.

We claim:

1. A compound of the formula:

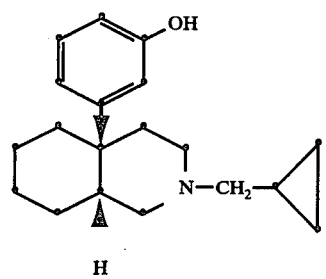

and its pharmaceutically-acceptable acid addition salts.

2. A compound according to claim 1, said compound being cis-dl-1-cyclopropylmethyl-3a-(m-hydroxyphenyl)-1,2,3,3a,4,5,6,7,7a,8-decahydroisoquinoline hydrochloride.

* * * * *